United States Patent [19]

Suzuki

[11] Patent Number: Plant 6,470

[45] Date of Patent: Dec. 20, 1988

[54] ROSE PLANT NAMED KOH-SAI

[75] Inventor: Seizo Suzuki, Tokyo, Japan

[73] Assignee: The Conard-Pyle Company, West Grove, Pa.

[21] Appl. No.: 13,038

[22] Filed: Feb. 10, 1987

[30] Foreign Application Priority Data

Feb. 24, 1986 [JP] Japan ..... 61-1808

[51] Int. Cl.[4] ..... A01H 5/00

[52] U.S. Cl. ..... Plt./20

[58] Field of Search ..... Plt./20

*Primary Examiner*—James R. Feyrer

*Attorney, Agent, or Firm*—Burns, Doane, Swecker & Mathis

[57] ABSTRACT

A new and distinct variety of Hybrid Tea rose plant is provided which continuously forms distinctive elegant fully double long-lasting blossoms which are brilliant scarlet red with a luminous yellow center. The foliage is very glossy and dark green in coloration. The new variety is very resistant to powdery mildew, and possesses an upright, vigorous and well-branched growth habit.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Fragrant Cloud variety (U.S. Plant Pat. No. 2,574). The male parent (i.e., the pollen parent) was the Kagayaki variety (non-patented). The parentage of the new variety can be summarized as follows:

Fragrant Cloud × Kagayaki.

The seeds resulting from the above pollination were sown and plantlets were obtained which were physically and biologically different from each other. Selective study resulted in the identification of a single plant of the new variety.

It was found that the new variety of Hybrid Tea rose plant of the present invention possesses the following combination of characteristics:

(a) when mature is upright, erect, and well-branched,
(b) exhibits a vigorous growth habit,
(c) forms regular very glossy dark green foliage,
(d) continuously forms attractive fully double long-lasting blossoms which are brilliant scarlet red with a luminous yellow center, and
(e) is very resistant to powdery mildew.

The new variety well meets the needs of the horticultural industry and is particularly well-suited for use in private and public gardens as an ornamental landscape plant. Also, the cut flowers are attractive indoors.

The characteristics of the new variety have been found to be strictly transmissible by vegetative propagation from one generation to another.

The new variety has been named the Koh-Sai variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were three years of age and were observed while growing outdoors at West Grove, Pa. during September when grafted on *Rosa froebelii* understock.

DETAILED DESCRIPTION

The chart used in the identification of the colors is that of The Royal Horticultural Society (R.H.S. Colour Chart). The description is based on observations made during September while grafted on *Rosa froebelii* understock and growing in the open air under normal field conditions at West Grove, Pa.

Class: Hybrid Tea.

Plant:

*Height.*—Approximately 130 to 140 cm.

*Habit.*—Upright, erect.

Branches:

*Color.*—Young stems: Deep bronze, Greyed-Red Group 181B. Mature flowering wood: Green Group 137A with bronze shadings.

Leaves:

*Petioles.*—Upper surface: Grooved, reddish-brown. Under surface: A few hooked prickles commonly are present.

*Leaflets.*—Number: 3 or 5 (most often). Shape: Ovate with base obtuse and apex acute. Serration: Simple and regular. General appearance: quite dense, dark, and very glossy. Color (fully expanded leaf on flowering stem): Upper surface: Green Group 132A. Under surface: Green Group 131B.

Inflorescence:

*Number of flowers.*—Generally one per stem.

*Peduncle.*—Fairly straight and rigid, approximately 6.5 to 7.5 cm. in length.

*Buds.*—Shape: Urn shaped at the reflexing of the sepals. Length: Approximately 3.2 to 3.5 cm. Color upon opening: Guard petals are Red Group 46A, under petals are Red Group 46B, the petal base is Yellow-Orange Group 21C suffused with Red.

*Flower.*—Fully double. Diameter: Approximately 9.5 to 12 cm. on average. Color (when opening begins): Upper surface: Red Group 44A, petal base suffused with Yellow-Orange Group 21C. Under surface: Red Group 46B with Yellow- Orange Group 21C at base. Color (when partially open): Upper surface: Red Group 44A, petal base suffused with Yellow-Orange Group 21C. Under surface: Red Group 46C, petal base suffused with Yellow-Orange Group 21C. Color (at end of opening): Upper surface: Red Group 46B, petal base Yellow-Orange Group 21C. Under surface: Red Group 46C, petal base Yellow-Orange Group 21C. Lasting quality: Long. Petal number: Commonly approximately 28 to 32 large petals, and 6 to 8 small petaloids at the center.

Development:

*Vegetation.*—Vigorous and regular.

*Flowering.*—Abundant and repeating.

*Disease resistance.*—Very resistant to powdery mildew, above average resistance to blackspot.

I claim:

1. A new and distinct variety of Hybrid Tea rose plant characterized by the following combination of characteristics:

(a) when mature is upright, erect and well-branched, (b) exhibits a vigorous growth habit, (c) forms regular very glossy dark green foliage, (d) continuously forms attractive fully double long-lasting blossoms which are brilliant scarlet red with a luminous yellow center, and (e) is very resistant to powdery mildew;

substantially as herein shown and described together with the parts thereof.

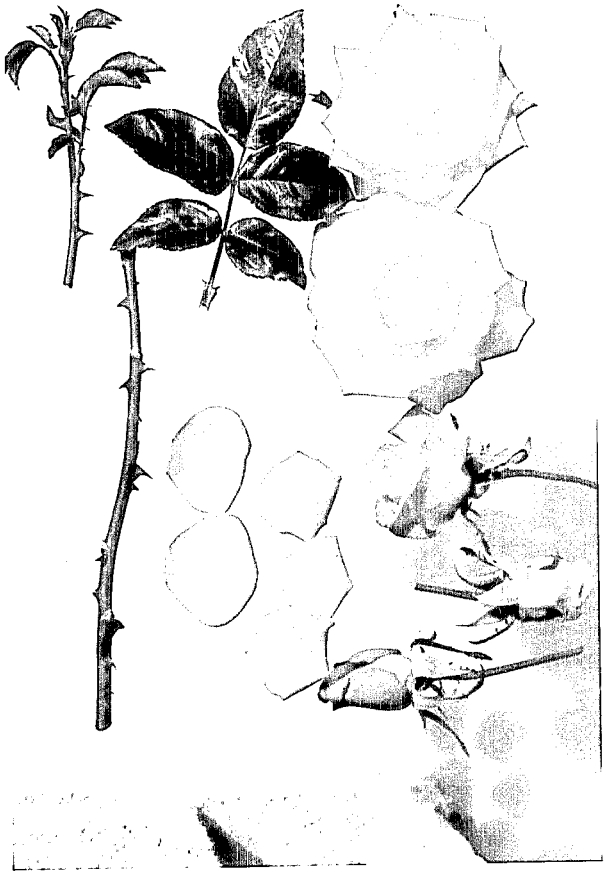

* * * * *